(12) United States Patent
Luo et al.

(10) Patent No.: US 10,329,335 B2
(45) Date of Patent: Jun. 25, 2019

(54) COMPOSITION AND SYSTEM FOR SEPARATING AND DETECTING ALPHA-FETOPROTEIN VARIANT AND USE THEREOF

(71) Applicant: BEIJING HOTGEN BIOTECH CO., LTD., Beijing (CN)

(72) Inventors: Haifeng Luo, Beijing (CN); Boan Li, Beijing (CN); Changqing Lin, Beijing (CN)

(73) Assignee: BEIJING HOTGEN BIOTECH CO., LTD., Beijing (CN)

( * ) Notice: Subject to any disclaimer, the term of this patent is extended or adjusted under 35 U.S.C. 154(b) by 0 days.

(21) Appl. No.: 15/541,178

(22) PCT Filed: Dec. 30, 2015

(86) PCT No.: PCT/CN2015/099774
§ 371 (c)(1),
(2) Date: Jun. 30, 2017

(87) PCT Pub. No.: WO2016/107576
PCT Pub. Date: Jul. 7, 2016

(65) Prior Publication Data
US 2018/0009863 A1    Jan. 11, 2018

(30) Foreign Application Priority Data
Dec. 31, 2014   (CN) .......................... 2014 1 0841397

(51) Int. Cl.
| C07K 14/47 | (2006.01) |
| G01N 33/68 | (2006.01) |
| G01N 33/543 | (2006.01) |
| A61K 38/17 | (2006.01) |
| G01N 30/06 | (2006.01) |

(52) U.S. Cl.
CPC ...... *C07K 14/4715* (2013.01); *A61K 38/1709* (2013.01); *G01N 33/54326* (2013.01); *G01N 33/68* (2013.01); *G01N 2030/065* (2013.01)

(58) Field of Classification Search
None
See application file for complete search history.

(56) References Cited

FOREIGN PATENT DOCUMENTS

| CN | 102147415 |   | 8/2011 |
| CN | 102147415 | A * | 8/2011 |
| CN | 102360014 |   | 2/2012 |
| CN | 102879567 |   | 1/2013 |
| CN | 103383374 |   | 11/2013 |
| CN | 104714026 |   | 6/2015 |
| CN | 204422547 |   | 6/2015 |
| EP | 2193372 |   | 6/2010 |
| WO | WO 2009/044985 |   | 4/2009 |

OTHER PUBLICATIONS

Fourth Office Action dated Sep. 20, 2017 with English translation from corresponding application No. CN 201510002936.2.
Supplemental EP Search Report dated Aug. 28, 2017 from corresponding application No. 15875252.7-1408 PCT CN/2015099774.
Liang Ru-Ping et al., "Magnetic Fe3O4@Au Composite-Enhanced Surface Plasmon Resonance for Ulstrasensitive Detection of Magnetic Nanoparticle-Enriched [Alpha]-Fetoprotein", Analytica Chimca ACTA, vol. 737, Aug. 2012 (Aug. 2012), pp. 22-28, XP002772913.
Ferreira Jose A., et al., "Synthesis and Optimization of Lectin Functionalized Nanoprobes for the Selective Recovery of Glycoprotiens from Human Body Fluids,", Analytical Chemistry Sep. 15, 2011, vol. 83, No. 18, Sep. 15, 2011 (Jun. 15, 2011) pp. 7035-1043, XP002772914, ISSN: 1520-6882.
Zhou, Hankun et al., "The Sandwich-Type Electrochemi Luminescence Immunosensor for Alpha-Fetoprotein Based on Enrichment by Fe2O4-Au Magnetic Nano Probes and Signal Amplification by CdS-Au Composite Nanoparticles Labeled anit-AFP", Analytica Chimica ACTA, vol. 746, Oct. 2012 (Oct. 2012), pp. 107-113, XP002772915.
Zhang Qian Yun et al., "Comparison of Chemiluminescence Enzyme Immunoassay Based on Magnetic Microparticles with Traditional Colorimetric ELISA for the Detection of Serum [Alpha]-Fetoprotein", Journal of Pharmaceutical Analysis 2012 Xi'An Jiaotong University CHN, vol. 2, No. 2, Apr. 2012 (Apr. 2012), pp. 130-135, XP002772916, ISSN: 2095-1779.
Database WPI, Week 201357, Thomson Scientific, London, GB; AN 2013-F97985 XP002772917, & CN 102 879 567 A (Tarcine Biomed Inc) Jan. 16, 2013 (Jan. 16, 2013).
Drake, Richard R., et al., "Lectin Capture Strategies Combined with Mass Spectrometry for the Discovery of Serum Glycoprotein Biomarkers,", Molecular & Ceullular Proteomics: MCP Oct. 2006, vol. 5, No. 10, Oct. 2006 (Oct. 2006), pp. 1957-1967, XP002772918, ISSN: 1535-9476.
Liao, Jian et al., "Serum Profiling Based on Fucosylated Glycoprotiens for Differentiating Between Chronic Hepatitis B and Hepatocellular Carcinoma", Biochemical and Biophysical Research Communications, vol. 420, No. 2, Apr. 2012 (Apr. 2012), pp. 308-314, XP002772919.
Korekane, Hiroaki et al., "Development of an Anitbidy-Lectin Enzyme Immunossay for Fucosylated [Alpha]-Fetopro", Biochimica et Biophysica Acta (BBA)—General Subjects, vol. 1820, No. 9, 312 Dec. 2011 (Dec. 31, 2011) pp. 1405-1411, XP028927534, ISSN: 0304-4165, DOI: 10.1016/J.BBAGEN, Dec. 15, 2011.
Wang, X. et al., "Development of High-Performance Magnetic Chemiluminescence Enzyme Immunoassay for Alpah Fetoprotein (AFP) in Human Serum", Clinica Chimica ACTA, Elsevier BV, Amsterdam, NL, vol. 393, No. 2, Jul. 17, 2008 (Jul. 17, 2008), pp. 90-94, XP022699939, ISSN: 0009-8981, DOI: 10.1016/J.CCA.2008.03.010 [retreived on Mar. 20, 2008].

(Continued)

*Primary Examiner* — Daniel C Gamett
(74) *Attorney, Agent, or Firm* — Hauptman Ham, LLP

(57) ABSTRACT

Disclosed are a composition and system for separating and detecting an alpha-fetoprotein variant, comprising a separation reagent and a detection reagent; a system for separating and detecting an alpha-fetoprotein variant and a use thereof; and a kit for separating and detecting the alpha-fetoprotein variant. By means of the composition and system for separating and detecting the alpha-fetoprotein variant, and the use thereof, primary liver cancer can be indicated early on, the sensitivity is high, and the method is rapid, simple and automated.

13 Claims, 2 Drawing Sheets

(56) References Cited

OTHER PUBLICATIONS

Zhang, Xiao-Feng et al., "Lens Culinaris Agglutinin-Reactive Fraction of Alpha-Fetoprotein as a Marker of Prognosis and a Monitor of Recurrence of Hepatocellular Carcinoma after Curative Liver Resection", Annals of Surgical Oncology, Springer-Verlag, NE, vol. 18, No. 8, Feb. 20, 2011 (Feb. 20, 2011) pp. 2218-2223, XP019926940, ISSN: 1534-4681, DOI: 10.1245/S10434-011-1613-7.

Yueping, Guan, et al., "Recent Developments of Magnetic Separation in Biotechnology Preparation of Magnetic Carries and Surface Chemical Modification", Journal of Chemical Industry and Engineering (China), Vla. 51 Suppl. Dec. 2000, pp. 315-319; 1994-2015 China Academic Journal of Electronic Publishing House, http://www.cnki.net.

"Immunological Technology and its Application"; Science Publishing, Beijing, 2010, CAO, Xuetao (Chief Editor); ISBN: 978-7-03-027340-6; 424 pages. http://www.lifescience.com.cn.

CN Office Action dated Mar. 8, 2016 with English translation from corresponding application No. CN 201510002936.2.

International Search Report and English translation from corresponding application No. PCT/CN2015/099774.

CN Office Action dated Oct. 20, 2016 with English translation from corresponding application No. CN 201510002936.2.

CN Office Action dated Apr. 1, 2017 with English translation from corresponding application No. CN 201510002936.2.

\* cited by examiner

COMPOSITION AND SYSTEM FOR SEPARATING AND DETECTING ALPHA-FETOPROTEIN VARIANT AND USE THEREOF

RELATED APPLICATIONS

The present application is a National Phase of International Application Number PCT/CN2015/099774, filed Dec. 30, 2015, and claims the priority of China Application 201410841397.7, filed Dec. 31, 2014.

TECHNICAL FIELD

The present invention relates to a composition, system, method for separating and detecting an alpha-fetoprotein variant and to use thereof, and meanwhile relates to a kit for separating and detecting an alpha-fetoprotein variant, which pertains to the field of medical equipment and in vitro diagnosis.

RELATED ART

Hepatocellular carcinoma (HCC) is the fourth most common malignancy in the world. Approximately 250,000 patients die each year from hepatocellular carcinoma, the pathogenesis of hepatocellular carcinoma remains unclear, and hepatocellular carcinoma has a high degree of malignancy in clinical practice and a mortality that ranks third among the digestive tract malignancies, so early detection and early treatment are a key to improve the survival rate of patients with hepatocellular carcinoma, while most patients are diagnosed with mid-advanced hepatocellular carcinoma when they are treated and lost the best treatment time. Risk factors for hepatocellular carcinoma include chronic hepatitis and liver cirrhosis caused by hepatitis B virus and hepatitis C virus. To get effective treatment, the clinical efficacy of screening and census of hepatocellular carcinoma depends on early diagnosis. HCC is an important type of tumor etiology, and it may be induced by chronic liver damage caused by liver cirrhosis, viral hepatitis, chemical carcinogens and environmental factors. HCC is highly malignant, easy to relapse and metastasis, and it has poor prognosis, and early diagnosis is quite difficult, so it is liable to delay the best treatment time.

Alpha-fetoprotein (AFP) is a glycoprotein, and the detection of blood AFP content is the most common means for diagnosing hepatocellular carcinoma so far. AFP can be synthesized from liver parenchymal cells and yolk sac cells in mammalian embryos, and a small amount of AFP can also be synthesized from gastrointestinal mucosal cells derived from endoderm. Under normal circumstances, AFP mainly exists in the fetal cycle, and AFP synthesis gradually reduces along with the development of the fetus. The serum AFP concentration in neonates may be 10 to 100 ng/ml at birth and decreases to normal adult level (less than 20 ng/ml) one year later after birth. If the AFP in a neonate significantly increases, it shows that the neonate suffers from neonatal hepatitis, congenital biliary atresia or an embryonic malignant tumor which can secrete AFP. There is a disadvantage of AFP as a diagnostic indicator of early liver cancer, i.e., a considerable proportion of liver diseases and cirrhosis diseases have positive results. AFP slight increase (20 to 200 ng/ml) is found in a considerable number of patients with chronic liver disease, and 11.7-44% of patients with cirrhosis are AFP positive. Hence, the value of AFP as a screening indicator for early liver cancer is significantly reduced in distinguishing benign liver disease and malignant liver tumors.

The structures of many oligosaccharide chains of AFP variants are not yet clear. At present, it is believed that the commonly known AFP variants refer specifically to AFP-L3 bound to *Lens culinaris* agglutinin (LCA). In 1999 the fourth session of the National Hepatology Conference, AFP-L3 was listed as one of the hepatocellular carcinoma markers which are clinical diagnostic criterias for primary hepatocellular carcinoma. In the Chinese Liver Cancer Diagnosis and Treatment Norms (2011), AFP-L3 is listed as a specific indicator for the diagnosis of hepatocellular carcinoma. Over the years, AFP-L3 has been recognized as a more specific primary hepatocellular carcinoma indicator than AFP alpha-fetoprotein alone.

AFP-L3 is the only protein produced by cancer cells in the patient's liver. A method for the detection of hepatocellular carcinoma using AFP-L3 was conducted in a multicenter, prospective, double-blind, and long-term clinical trial in Canada and the United States. The study showed that patients with elevated AFP-L3 (15% or more) had a 7-fold increase in the risk of suffering from hepatocellular carcinoma in the next 21 months. According to the existing "Guidelines for the Practice of Hepatocellular Carcinoma Oncology", the incidence of hepatocellular carcinoma in these patients is extremely high.

Clinical significance of AFP variant detection:

1) Identification of hepatocellular carcinoma and benign liver diseases. Patients with primary hepatocellular carcinoma often have elevated AFP, but many benign liver diseases may also be associated with elevated AFP, so it is sometimes difficult to distinguish between a benign liver disease and malignant lesions based only on the AFP detection results. In this case, AFP variant detection has a good clinical significance, it is more valuable especially for AFP content in the range of 30-400 ng/ml. Sato et al. completed a prospective study of 361 cases (Early recognition of hepatocellular carcinoma based on altered pro les of alpha-fetoprotein, Sato, Y., et al., N. Engl. J. Med., 328,1802-1806, 1993), AFP-L3% detection and a 35-month follow-up was conducted in 361 patients with chronic hepatitis B and hepatitis C. During the study, liver cancer was developed in 24 (73%) of 33 patients with AFP-L3% higher than baseline. AFP-L3% can be used as an indicator of distinguishing liver cancer patients from patients with liver cirrhosis and can be used as a predictive index elevated 3 to 18 months before the diagnosis by imaging techniques.

2) Monitoring after surgery of hepatocellular carcinoma. After resection of hepatocellular carcinoma, serum AFP content decreases, and the rate of decline depends on the amount and half-life of residual AFP, and it usually becomes negative in two months, and AFP variant disappears when the result becomes negative. If the AFP decreases significantly but is not negative, and the change of AFP variant is not obvious, it suggests that the surgery is not complete, and there may be residual margins, vascular cancer bolt, satellite nodules or metastasis. If the percentage of AFP variant in the total AFP decreases to 25% or less, and the concentrations of AFP and the AFP variant are relatively constant, this may be caused by hepatitis or cirrhosis.

3) Embryonic dysplasia and fetal congenital disorders. In a normal gestational period, AFP in the maternal serum is in equilibrium with AFP in the embryo. In case of fetal malformations or placental barrier abnormalities, fetal serum can penetrate into the amniotic fluid or the amniotic fluid can penetrate into the maternal serum, resulting in sharp increase in maternal amniotic fluid or serum AFP. However, measurement of only the total amount of AFP has some limitations. Experiments show that AFP and/or AFP variant may be positive in case of neural tube defects, anencephalus or rachischisis and so on, pediatric hepatoblastoma, biliary atresia, gonadal tumor, malignant teratoma, etc.

Currently methods used for detecting AFP variant include plant lectin affinity chromatography, polyacrylamide gel electrophoresis, affinity blotting method, affinity cross immunoelectrophoresis, etc. These methods can directly separate the AFP-L3 protein and perform quantitative estimation. According to the final detection methods, they can be divided into:

Coomassie brilliant method: After electrophoresis, the sample is directly stained with Coomassie brilliant blue, and the peak is observed after elution. This method is simple, but there are many interference factors, and the sensitivity thereof is about 1000 ng/ml.

Enzyme labeled method: the sample after electrophoresis and a peroxidase labeled antibody are incubated and developed with diaminobenzidine after rinse. The detection sensitivity can be increased to 50 ng/ml.

Gold and silver staining method: the sample after electrophoresis is directly incubated with *staphylococcus aureus* protein A2 gelatin, and then is developed with a silver coloring solution, to obtain a clear peak, and the sensitivity can reach 32 ng/ml.

Autoradiography: the most commonly used detection method in China so far, the sensitivity thereof can be 31 ng/ml. The principle is as follows: the sample is separated and electrophoresed in a gel containing a lectin, and then is electrophoresed after addition of iodine 125-labeled AFP, followed by secondary electrophoresis in an anti-AFP antibody gel; after the electrophoresis, the gel is dried and covered with an X-ray film, which are exposed, and the image is rinsed. The entire experimental process is complicated. For a long time, only a few clinical laboratories in China have been able to measure AFP variants, and a few cities can meet the requirements of clinical measurement of AFP variants, and there is no relevant domestic reagent supply.

Besides, at present, AFP-L3 is isolated mainly by centrifugal tube separation method in China. The method uses agarose-coupled LCA, separates AFP-L3 by centrifugation, and then conducts detection with an AFP detection reagent. Centrifugal tube separation method is so far the only method for detecting AFP-L3 percentage approved by the State Food and Drug Administration in China.

The existing methods for measuring the percentage of alpha-fetoprotein variant comprise many manual operation procedures and cumbersome steps, they require more equipment and are time-consuming, and they cannot be automated. Hence, high-throughput sample detection cannot be realized, and they are greatly impacted by manual operation, which finally causes deviation of the detection results.

SUMMARY

In order to overcome the deficiencies of the prior art, the present invention provides a composition, system, method for separating and detecting an alpha-fetoprotein variant and to use thereof, which obtains a percentage of the alpha-fetoprotein variant by detecting the alpha-fetoprotein variant content and alpha-fetoprotein content in a blood sample.

A separation and detection composition for an alpha-fetoprotein variant AFP-L3 provided in this disclosure comprises a separation reagent and a detection reagent; the separation reagent comprises magnetic particle coupling a lectin, and an eluent; the magnetic particle coupling the lectin are used to specifically bind to AFP-L3 in the sample to be detected; the detection reagent comprises magnetic particle coated with an anti-alpha-fetoprotein antibody and an enzyme-labeled anti-alpha-fetoprotein antibody.

In one preferable embodiment, the anti-alpha-fetoprotein antibody is a monoclonal antibody against alpha-fetoprotein. In one more preferable embodiment, the anti-alpha-fetoprotein antibody is: an anti-alpha fetoprotein monoclonal antibody with an item number A8452 manufactured by Sigma Co., Ltd., or an anti-alpha-fetoprotein antibody with an item number HPA023600 manufactured by Sigma Co., Ltd.

In one preferable embodiment, the separation reagent further comprises a protective solution for increasing the stability of the separation reagent and improving the separation efficiency. Preferably, the protective solution is 0.02 M PBS, 0.5% BSA, pH 7.4 and 0.1 M D-mannoside.

In one preferable embodiment, the detection reagent further comprises a buffer for increasing the stability of the detection reagent, improving the detection sensitivity and detection specificity. Preferably, the buffer is 0.02 M PBS, 10% bovine serum, 0.1% proclin-300.

In one preferable embodiment, the separation reagent and/or detection reagent further comprises a cleaning solution for improving the binding efficiency, reducing nonspecific adsorption, improving the sensitivity of separation and detection. Preferably, the cleaning solution in the separation reagent is 20 mM Tris-HCl and 0.5 M D-mannoside, and the cleaning solution in the detection reagent is a 1% Tween 20 solution prepared in PBS pH 7.4.

In one preferable embodiment, in the magnetic particle coupling a lectin, the lectin includes *lens culinaris* agglutinin and/or concanavalin lectin.

In one preferable embodiment, in the magnetic particle coupling a lectin, a polymer component covering the magnetic particle includes silicides, polysaccharides, proteins, cellulose or resins.

In one preferable embodiment, the separation and detection composition is provided in form of a card or strip.

The present invention further provides a separation and detection kit for alpha-fetoprotein variant, comprising the aforesaid separation and detection composition.

The present invention further provides a separation and detection system for alpha-fetoprotein variant, comprising:

a magnetic separation module for separating magnetic particle from a liquid, the magnetic separation module being used in conjunction with a separation reagent and a detection reagent;

a detection module for detecting an alpha-fetoprotein variant and an alpha-fetoprotein content;

a data processing module for calculating a ratio of the alpha-fetoprotein variant to the alpha-fetoprotein; and any one of the aforesaid separation and detection composition or the aforesaid kit.

The magnetic separation module cooperates with the separation reagent in the separation and detection composition for accomplishing the separation of alpha-fetoprotein variant.

The magnetic separation module cooperates with the detection reagent in the separation and detection composition for accomplishing the detection of the alpha-fetoprotein variant content and alpha-fetoprotein content.

In a preferable embodiment, when it is selected to detect the alpha-fetoprotein content, the magnetic separation module does not cooperate with the separation reagent, and the detection means detects the content of alpha-fetoprotein in a sample to be detected;

when it is selected to detect the alpha-fetoprotein variant content, the magnetic separation module cooperates with the separation reagent to separate the alpha-fetoprotein variant in a sample to be detected, and the detection means detects the content of alpha-fetoprotein variant in the sample to be detected;

when it is selected to detect a percentage of the alpha-fetoprotein variant, the magnetic separation module separates the alpha-fetoprotein variant in a sample to be detected, the detection module detects respectively the content of alpha-fetoprotein variant and the content of the alpha-fetoprotein in the sample to be detected, and the data processing module calculates the percentage of the alpha-fetoprotein variant, i.e., a percentage (AFP-L3%) of the alpha-fetoprotein variant (AFP-L3) with respect to the total alpha-fetoprotein (AFP).

The present invention finally provides a method for separating and detecting an alpha-fetoprotein variant, and a use of the aforesaid separation and detection composition or the aforesaid separation and detection system in separating and detecting the alpha-fetoprotein variant.

In one preferable embodiment, the method for separating and detecting an alpha-fetoprotein variant comprises:

separating alpha-fetoprotein variant AFP-L3 from alpha-fetoprotein by a separating method, and detecting the separated alpha-fetoprotein variant AFP-L3; wherein the separating method is mainly binding lectin-labeled magnetic particles to alpha-fetoprotein variant AFP-L3 in a sample; then the alpha-fetoprotein variant AFP-L3 is separated by the magnetic particle, and the separated alpha-fetoprotein variant AFP-L3 is obtained by a corresponding eluting method; the separated sample is subjected to AFP detection by using an AFP immunoassay method, and the obtained AFP result is just the result of AFP-L3.

In one preferable embodiment, the lectin-labeled magnetic particle is agarose-coated magnetic particle labeled with *lens culinaris* agglutinin (LCA), agarose-coated paramagnetic particle which can be combined with the alpha-fetoprotein variant.

In one preferable embodiment, the AFP immunoassay method is a magnetic particle chemiluminescence method.

As compared with the prior art, the present invention has the following advantages: the operator can complete the detection only within 30 minutes by simply adding the sample and so on; meanwhile, the method can quantitatively calculate the content of alpha-fetoprotein and alpha-fetoprotein variant contained in a blood sample directly by means of detection and meanwhile obtain AFP-L3%; this method is simple, the detection is fast and convenient, the results are accurate, and the sensitivity is high, and this method is automated and provides support for the prevention, diagnosis and treatment of liver cancer.

Wherein, 1—a sample well; 2—a reagent tank containing magnetic particle coupling a lectin; 3—a reagent tank containing an eluent; 4—a reagent tank containing magnetic particle coated with an anti-alpha-fetoprotein antibody; 5—a reagent tank containing an enzyme-labeled anti-alpha-fetoprotein antibody; 6—a reaction well; 7—a reagent card.

Figure 1:
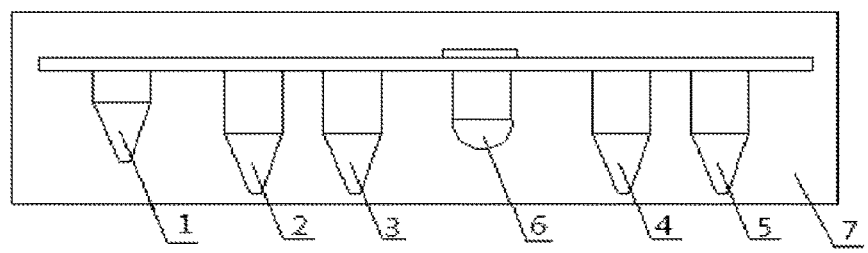
FIG. 1 is a schematic diagram of an alpha-fetoprotein variant separating and detecting composition according to the present invention, provided in form of card.
Figure 2:
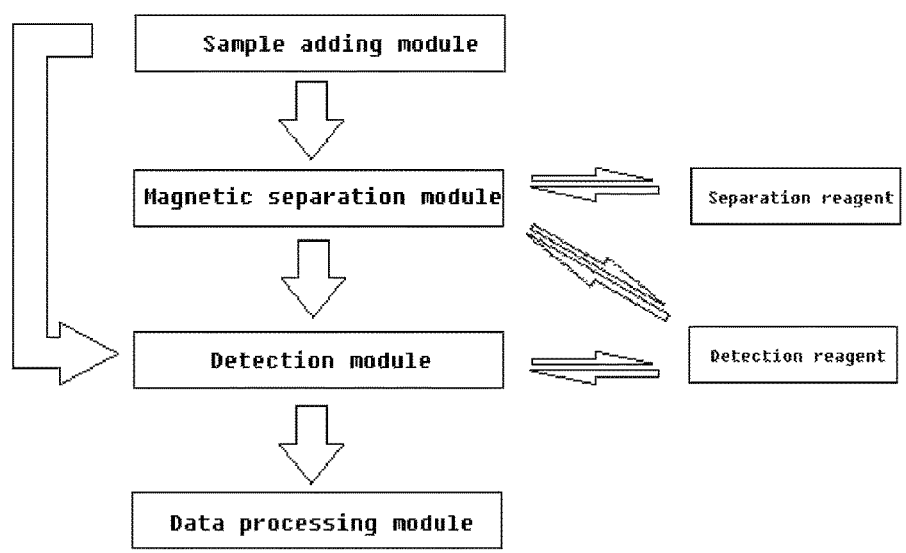

FIG. 2 is a schematic diagram of an alpha-fetoprotein variant separating and detecting system according to the present invention.

Figure 3:
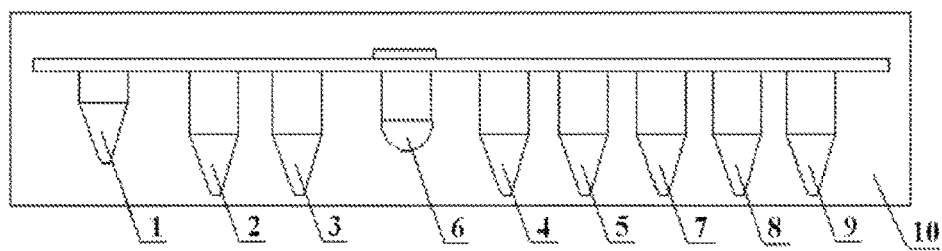

FIG. 3 is a schematic diagram of one detailed embodiment of the alpha-fetoprotein variant separating and detecting system according to the present invention. Wherein, 1—a sample well; 2—a reagent tank for pre-dispensing magnetic particle coupling a lectin; 3—a reagent tank for pre-dispensing AFP-L3 cleaning solution; 4—a reagent tank for pre-dispensing AFP-L3 eluent; 5—a reagent tank for pre-dispensing magnetic particle coated with an anti-alpha-fetoprotein antibody (anti-AFP-1); 6—a reaction well; 7—a reagent tank for pre-dispensing an enzyme-labeled anti-alpha-fetoprotein antibody (anti-AFP-2); 8—a reagent tank for pre-dispensing an AFP cleaning solution; 9—a reagent tank for pre-dispensing a Luminol substrate; 10—a reagent card.

DETAILED EMBODIMENTS

The present invention will be described in detail with reference to the drawings and examples. It should be understood that the specific examples described here only for illustrating the present invention and are not used for limiting the scope of the present invention.

EXAMPLE 1

A separation and detection composition for an alpha-fetoprotein variant provided by the present invention comprises a separation reagent and a detection reagent for detecting a percentage of the alpha-fetoprotein variant.

The separation reagent comprises magnetic particle coupling a lectin, and an eluent; the magnetic particle coupling the lectin are used to specifically bind to AFP-L3 in a sample to be detected; the detection reagent comprises magnetic particle coated with an anti-alpha-fetoprotein antibody and an enzyme-labeled anti-alpha-fetoprotein antibody. The major components of the aforesaid reagents and preparation methods thereof are as follows.

In the magnetic particle coupling a lectin, the lectin is *lens culinaris* agglutinin (LCA), concanavalin lectin, or *lens culinaris* agglutinin (LCA) and concanavalin lectin.

The magnetic particle is activated ferriferrous oxide superparamagnetic nanoparticle that are coated with an epoxy resin and have a size of 1 micron (hereinafter referred to as magnetic particle) and *lens culinaris* agglutinin (LCA) from Sigma company.

1. The lectin and the magnetic particle is coupled through the following steps:

1) Weigh 2 mg of LCA and dissolve it in 7.5 mL of a coupling buffer (0.1 mmol/L $NaHCO_3$, pH 8.3, 0.5 mol/L NaCl), combine it with 1.5 g of washed magnetic particle, mix them up and down in a plugged 10 mL tube (mix at room temperature for 2 h);

2) Wash uncoupled LCA with 10 mL of the coupling buffer. Based on the measured LCA content in the washing solution, the coupling rate was 98%;

3) Block the remaining activated groups with 0.2 mol/L glycine;

4) Perform washing three times with 10 mL 0.1 mol/L acetic acid buffer (pH 4, containing 0.5 mol/L NaCl) and 0.1 mol/L Tris buffer (pH 8, containing 0.5 mol/L NaCl), followed by washing once with 0.1% BSA and 0.1 mmol/L PBS (PBS-BSA) of $CaCl_2$, temporarily reserve at 4° C.

The aforesaid magnetic particle coated with an epoxy resin may be replaced with magnetic particle coated with materials such as titanium silicide, polystyrene, dextran, agarose, sulfonamide resin, bovine serum albumin, biotin.

2. Magnetic particle coated with alpha-fetoprotein antibody:

Wherein, for the alpha-fetoprotein antibody, an anti-alpha fetoprotein monoclonal antibody with an item number A8452 manufactured by Sigma company was used as anti-alpha fetoprotein antibody 1 (anti-AFP-1). The preparation method is as follows.

1) Activation of the magnetic particle
   a. suck 50 ml magnetic particles (10% W/V);
   b. wash the magnetic particles with an equal volume of 50 mM MES buffer;
   c. re-suspend the magnetic particles with an equal volume of 100 mM MES buffer;
   d. add an activating reagent carbodiimide (EDC) to a final concentration of 0.04 g/ml;
   e. vibrate to perform activation at room temperature for 1 h.

2) Coating of the magnetic particles with an anti-alpha-fetoprotein antibody 1 (anti-AFP-1)
   a. after the activation ends, apply a magnetic field and discard the supernatant;
   b. wash the activated magnetic particles with 10 times the volume of 50 mM MES;
   c. add 0.2 mg of anti-alpha-fetoprotein antibody 1;
   d. vibrate to carry out reaction at room temperature for 3 h.

3) Termination of the coating of the magnetic particles with an anti-alpha-fetoprotein antibody 1 (anti-AFP-1)
   a. after the reaction ends, apply a magnetic field and discard the supernatant;
   b. add 10 times the volume of a coating terminating solution;
   c. vibrate to carry out reaction at room temperature for 3 h.

4) Cleaning and preservation of the anti-alpha-fetoprotein antibody 1 (anti-AFP-1) magnetic particles
   a. after the reaction ends, apply a magnetic field and discard the supernatant;
   b. add 10 times the volume of a coating cleaning solution, of which the main ingredients are 0.02 M PBS, 0.5% Tween-20, 100 mM NaCl, repeatedly clean four times;
   c. preserve the anti-alpha-fetoprotein antibody 1 (anti-AFP-1) magnetic particles with 10 times the volume of a magnetic particle preservation solution (pH 7.4, 0.02 M PBS, 0.5% BSA, 2% sucrose, 0.2% Tween-20, 0.2% PC-300).

3. Enzyme-labeled anti-alpha-fetoprotein antibody

A peroxidase (HRP) from Sigma company was coupled with an anti-alpha-fetoprotein antibody with an item number HPA023600 from Sigma company, to form an anti-alpha-fetoprotein antibody 2 (anti-AFP-2). The preparation method is as follows.

1) Oxidation of enzyme (keep dark during the whole process)
   a. weigh 5 mg HRP, dissolve it with 250 µl of ddH$_2$O;
   b. weigh 5 mg NaIO$_4$, dissolve it with 250 µl of ddH$_2$O to a concentration of 20 mg/ml;
   c. add the NaIO$_4$ solution dropwise to the HRP solution while stirring;
   d. place the mixed solution at 4° C., stand for 30 minutes;
   e. weigh 5 ml of ethylene glycol and dissolve it in 25 µl of ddH$_2$O, and add the resulting solution dropwise to the above mixed solution while stirring;
   f. stand for 30 minutes at room temperature;
   g. The oxidation of enzyme finished, and the final HRP concentration was 10 mg/ml.

2) Preparation and labeling of the anti-alpha-fetoprotein antibody 2 (anti-AFP-2) (keep dark):
   a. adjust the anti-alpha-fetoprotein antibody concentration to about 5 mg/ml (concentrate with PEG 20000 if the protein concentration was too low), perform dialysis to remove glycerol or impurities (such as Tris) with 50 mmol/L CB at about pH 9.5 (mix 1 mol/L NaHCO$_3$ with 1 mol/L Na$_2$CO$_3$ at a ratio of 10:1, dilute the mixture 20 times with a distilled water before use), perform dialysis overnight at 4° C., while exchanging the liquid three times;
   b. mix the anti-alpha-fetoprotein antibody 2 (anti-AFP-2) and HRP at a ratio of 1:4, and subject the mixture to dialysis in 50 mmol/L pH 9.5 CB for 6 hours or more, while exchanging the liquid once in the first two hours;
   c. terminate the reaction with 0.2 ml of freshly prepared 5 mg/ml NaBH$_4$ solution, shake well, and stand at 4° C. for 2 hours, while shaking every half hour;
   d. perform dialysis overnight with 10 mM PBS at pH 7.2 (prepare a 0.01 mol/L stock solution of Na$_2$HPO$_4$ and NaH$_2$PO$_4$, mix them evenly to form a PBS buffer according to the desired pH), while exchanging the liquid once.

3) Subpackage: dilute the HRP enzyme labeled anti-alpha-fetoprotein antibody 2 (anti-AFP-2) obtained in step 2) to 1 mg/ml (calculated based on the initial antibody concentration) with a buffer containing 10% fetal bovine serum, of which the main ingredients are 0.02M PBS, 10% fetal bovine serum, 3% sucrose, 0.2% Tween-20, etc., subpackage and store at 4° C.

4. Step of separating the alpha-fetoprotein variant by using the magnetic particles coupling the lectin in this example:

1) add 50 µl of 1% magnetic particles coupling the lectin and 200 µl of serum samples to be tested in the same tube, mix well and stand for 5 minutes;

2) adsorb the magnetic particles at the bottom of the tube with a magnet, and then absorb the supernatant and discard it;

3) remove the magnet, add 500 µl of an AFP-L3 cleaning solution, mix well to ensure that the magnetic particles are completely suspended;
   the AFP-L3 cleaning solution: 0.02 M PBS (pH 7.0), 0.5% Tween-20;

4) adsorb the magnetic particles at the bottom of the tube with a magnet, and then absorb the supernatant and discard it;

5) repeat steps 3), 4) twice, and wash the magnetic particles;

6) remove the magnet, add 200 µl of an AFP-L3 eluent, mix well to ensure that the magnetic particles are completely suspended, stand for 10 minutes;
   AFP-L3 eluent: 0.02 M PBS (pH 7.0), 5 M D-mannoside, or 20 mm Tris-HCl, NaCl 150 mm, pH 7.4 buffer, which containing 500 mm α-methyl-D-mannoside, 0.1% Proclin 300;

7) adsorb the magnetic particles at the bottom of the tube with a magnet, to obtain the supernatant which is a liquid of the separated alpha-fetoprotein variant AFP-L3.

5. Step of detecting AFP by using the magnetic particles coated with anti-alpha-fetoprotein antibody (anti-AFP-1) and an HRP enzyme-labeled anti-alpha-fetoprotein antibody 2 (anti-AFP-2) in this example:

1) add 50 µl of 1% magnetic particles coated with anti-alpha-fetoprotein antibody (anti-AFP-1) in an assay tube, add 50 µl of a sample to be detected at the same time, followed by addition of 50 µl of 1000-fold diluted HRP enzyme-labeled anti-alpha-fetoprotein antibody 2 (anti-AFP-2), mix well, and perform incubation at 37° C. for 5 minutes;

2) adsorb the magnetic particles at the bottom of the tube with a magnet, and then absorb the supernatant and discard it;

3) remove the magnet, add 500 μl of an AFP cleaning solution, mix well to ensure that the magnetic particles are completely suspended;

the AFP cleaning solution: 0.02 M PBS (pH 7.0), 0.5% Tween-20;

4) adsorb the magnetic particles at the bottom of the tube with a magnet, and then absorb the supernatant and discard it;

5) repeat steps 3), 4) twice, and wash the magnetic particles;

6) remove the magnet, add 100 μl of a Luminol substrate, mix well to ensure that the magnetic particles are completely suspended, perform incubation at 37° C. for 1 minute;

7) measure the intensity of a luminescence signal on a chemiluminescence analyzer, and calculate the content of AFP in the sample according to a standard curve.

6. Step of detecting AFP-L3 in this example:

1) add 50 μl of 1% magnetic particles coupling the lectin and 200 μl of serum samples to be tested in the same tube, mix well and stand for 5 minutes;

2) adsorb the magnetic particles at the bottom of the tube with a magnet, and then absorb the supernatant and discard it;

3) remove the magnet, add 500 μl of an AFP-L3 cleaning solution, mix well to ensure that the magnetic particles are completely suspended;

the AFP-L3 cleaning solution: 0.02 M PBS (pH 7.0), 0.5% Tween-20;

4) adsorb the magnetic particles at the bottom of the tube with a magnet, and then absorb the supernatant and discard it;

5) repeat steps 3), 4) twice, and wash the magnetic particles;

6) remove the magnet, add 200 μl of an AFP-L3 eluent, mix well to ensure that the magnetic particles are completely suspended, stand for 10 minutes;

AFP-L3 eluent: 0.02 M PBS (pH 7.0), 5 M D-mannoside, or 20 mm Tris-HCl, NaCl 150 mm, pH 7.4 buffer, which containing 500 mm α-methyl-D-mannoside, 0.1% Proclin 300;

7) adsorb the magnetic particles at the bottom of the tube with a magnet, to obtain the supernatant which is a liquid of the separated alpha-fetoprotein variant AFP-L3;

8) add 50 μl of 1% magnetic particles coated with anti-alpha-fetoprotein antibody (anti-AFP-1) in an assay tube, add 50 μl of the liquid obtained in 7) at the same time, followed by addition of 50 μl of 1000-fold diluted HRP enzyme-labeled anti-alpha-fetoprotein antibody 2 (anti-AFP-2), mix well, and perform incubation at 37° C. for 5 minutes;

9) adsorb the magnetic particles at the bottom of the tube with a magnet, and then absorb the supernatant and discard it;

10) remove the magnet, add 500 μl of an AFP cleaning solution, mix well to ensure that the magnetic particles are completely suspended;

the AFP cleaning solution: 0.02 M PBS (pH 7.0), 0.5% Tween-20;

11) adsorb the magnetic particles at the bottom of the tube with a magnet, and then absorb the supernatant and discard it;

12) repeat steps 3), 4) twice, and wash the magnetic particles;

13) remove the magnet, add 100 μl of a Luminol substrate, mix well to ensure that the magnetic particles are completely suspended, perform incubation at 37° C. for 1 minute;

14) measure the intensity of a luminescence signal on a chemiluminescence analyzer, and calculate the content of AFP in the detected sample according to a standard curve.

7. Step of detecting a percentage (AFP-L3%) of the alpha-fetoprotein variant in this example:

1) detect the alpha-fetoprotein AFP content in the sample according to the above item 5;

2) detect the alpha-fetoprotein variant AFP-L3 content in the sample according to the above item 6;

3) divide the alpha-fetoprotein variant AFP-L3 content calculated in 2) by the alpha-fetoprotein AFP content, to obtain the percentage (AFP-L3%) of the alpha-fetoprotein variant.

The separation and detection composition described in this example was used to perform detection of the AFP content:

An AFP detection kit (electrochemiluminescence method) manufactured by Roche company was used as a control group, to compare the accuracy of AFP content detection results. The cutoff value of AFP content is 20 μg/L, so results higher than 20 μg/L were positive results, and results lower than 20 μg/L were negative results. The detection results are shown in Table 1:

|  | Positive samples 198 | Negative samples 254 |
| --- | --- | --- |
| Roche AFP detection kit | 198 | 254 |
| This example | 198 | 254 |

The detection results show that the sensitivity and specificity of this example reached 100% in 452 samples detected.

The separation and detection composition described in this example was used to detect a percentage of AFP-L3:

An alpha-fetoprotein variant separation tube manufactured by Beijing Hotgen Biotech CO., Ltd., of which the product registration certificate number is No. 3401646 from 2014 (approved) by State Food and Drug Administration, was used while using an AFP detection kit (electrochemiluminescence method) manufactured by Roche company was used as a control group, to compare the accuracy of AFP-L3 percentage detection results. The cutoff value of AFP-L3 percentage is 10%. The detection results are shown in Table 2:

TABLE 2

|  | Positive samples 107 | Negative samples 172 |
| --- | --- | --- |
| Roche AFP detection kit (electrochemiluminescence method) | 107 | 172 |
| This example | 107 | 169 |

As compared with the control group, AFP-L3 percentage of 107 samples, of which the AFP-L3 percentage was positive in the detection of the control group, was also positive in the detection of this example; among 172 samples of which the AFP-L3 percentage was negative in the detection of the control group, 169 samples had negative results in the detection of this example. For the other three samples, after comparing the clinical diagnosis, it was found that the patients were patients with early primary hepatocellular carcinoma. As shown by the detection results, the separation and detection composition described in this example was more sensitive than the detection performance of the control group, for which the reason should be that the AFP-L3 protein separation efficiency is improved so that it is possible to more accurately detect AFP-L3 percentage in the sample.

EXAMPLE 2

A separation and detection composition for an alpha-fetoprotein variant provided by the present invention according to the separation and detection composition for an alpha-fetoprotein variant provided in Example 1, wherein the separation reagent may further comprise a protective solution, and the detection reagent may further comprise a buffer.

The separation reagent and the detection reagent may comprise a cleaning solution, respectively.

Major ingredients of the aforesaid reagents are as follows:
the protective solution: 0.02 M PBS, 0.5% BSA, pH 7.4, 0.1 M D-mannoside,
the buffer: 0.02 M PBS, 10% bovine serum, 0.1% proclin-300,
the cleaning solution in the separation reagent: 20 mM Tris-HCl, 0.5 M D-mannoside,
the cleaning solution in the detection reagent: 1% Tween 20 solution prepared by PBS pH 7.4.

The above-mentioned D-mannoside can be replaced with carbohydrates such as fucose, fructose, sucrose and trehalose.

EXAMPLE 3

A separation and detection system for an alpha-fetoprotein variant provided by the present invention is used for detecting a percentage of the alpha-fetoprotein variant. As shown by FIG. 2,
it comprises a magnetic separation module for separating the alpha-fetoprotein variant, a detection module for detecting an alpha-fetoprotein variant content and an alpha-fetoprotein content, and a data processing module for calculating a ratio of the alpha-fetoprotein variant to the alpha-fetoprotein. Preferably, the separation and detection system may further comprise a sampling module, and the data processing module may further comprise an optical signal reading device, preferably a photon counting probe with model number H10682-110 or a photomultiplier tube with model number R1166 manufactured by Nippon Hamamatsu Photonics Co. Ltd.

The reagent card comprises the separation and detection composition described in Example 1, which is pre-dispensed into a plurality of reagent tanks on the reagent card, to carry out the reaction, each reagent having at least one reagent tank. The reagent card comprises a sample well, a separation reagent tank, a detection reagent tank and a reaction well, and the reagent card in this example, as shown in FIG. 3, has a constitution as follows:
1. a sample well; 2. a reagent tank for pre-dispensing magnetic particles coupling a lectin; 3. a reagent tank for pre-dispensing AFP-L3 cleaning solution; 4. a reagent tank for pre-dispensing AFP-L3 eluent; 5. a reagent tank for pre-dispensing magnetic particles coated with an anti-alpha-fetoprotein antibody (anti-AFP-1); 6. a reaction well; 7. a reagent tank for pre-dispensing an enzyme-labeled anti-alpha-fetoprotein antibody (anti-AFP-2); 8. a reagent tank for pre-dispensing an AFP cleaning solution; 9. a reagent tank for pre-dispensing a Luminol substrate.

Wherein, wells b, c, d together compose a magnetic separation module, and all the reagents therein may be used for accomplishing the separation of alpha-fetoprotein variant; wells e, f, g, h, I together compose a detection module, and all the reagents therein may be used for accomplishing the detection of the concentration of AFP added to the sample.

The use of the detection module alone can accomplish detection of AFP content in the sample; the use of the separation module and the detection module in combination can accomplish separation of alpha-fetoprotein variant AFP-L3 in the sample and detection of the AFP-L3 content. Then, a percentage of the alpha-fetoprotein variant is obtained by dividing the AFP content by the AFP-L3 content.

The sample to be detected was detected in the method described in this example, and the detection results are shown in Table 3:

| | | Positive rate | |
| --- | --- | --- | --- |
| Sample background | number | AFP ($\geq$=20 ng/ml) | AFP-L3% ($\geq$=10%) |
| Primary hepatocellular carcinoma | 216 | 100% | 92% |
| Healthy people | 324 | 0 | 0 |
| liver cirrhosis | 105 | 100% | 5% |
| liver hepatitis | 174 | 100% | 3% |
| other cancers* | 63 | 8% | 0% |

*Other cancers include esophageal cancer, lung cancer, leukemia.

As shown by the results, the present invention achieved a positive rate of 92% to primary hepatocellular carcinoma, a specificity of 100% to healthy people, and a specificity of 95% and 97% respectively to liver cirrhosis and liver hepatitis, and a specificity of 0% to other cancers.

EXAMPLE 4

The separation and detection system for an alpha-fetoprotein variant provided according to Example 3 further comprises a detection setting module, which comprises an alpha-fetoprotein content measurement unit, an alpha-fetoprotein variant content measurement unit, and a unit for measuring percentage of alpha-fetoprotein variant.

When the alpha-fetoprotein content measurement unit was selected, the magnetic separation module did not take part in the treatment of a sample to be detected, and the detection means detected the content of alpha-fetoprotein in the sample to be detected.

When the alpha-fetoprotein variant content measurement unit was selected, the magnetic separation module separated the alpha-fetoprotein variant in the sample to be detected, the detection module detects the content of alpha-fetoprotein variant and the content of alpha-fetoprotein in the sample to be detected, and the data processing module calculates a percentage of the alpha-fetoprotein variant.

EXAMPLE 5

The separation and detection system for an alpha-fetoprotein variant provided according to Example 3 or 4 employs the separation and detection composition described in Example 2 instead of the separation and detection composition described in Example 1.

EXAMPLE 6

The method for separating and detecting an alpha-fetoprotein variant provided by the present invention employs the aforesaid separation and detection system to detect a percentage of an alpha-fetoprotein variant, comprising the following steps:

1) adding sample add a sample of hemolytic serum, plasma, or whole blood to the separation and detection system or added to the sample wells provided by the aforesaid reagent card;

2) separating the alpha-fetoprotein variant add the sample to a reaction cup containing magnetic particle coupling a lectin, shake well;

concentrate the magnetic particle by a magnetic separation module and discard the liquid;

add an eluent to the reaction cup in which the magnetic particle has been concentrated, shake well, and concentrate the magnetic particles by the magnetic separation module, to obtain an alpha-fetoprotein variant eluent;

3) incubation add the alpha-fetoprotein variant eluent to a reaction cup containing magnetic particle coated with alpha-fetoprotein monoclonal antibody, and meanwhile add an enzyme-labeled anti-alpha-fetoprotein antibody to the reaction cup, to undergo incubation;

4) concentration and cleaning concentrate the magnetic particle by the magnetic separation module, and discard the liquid; add a cleaning solution to the reaction cup, shake well, and then concentrate the magnetic particle by the magnetic separation module once again, and discard the liquid;

5) color development add the concentrated magnetic particle to a luminol substrate, and obtain a concentration of alpha-fetoprotein heterosomes by a data processing module;

6) at the same time with 2), add a sample to the reaction cup, and add magnetic particle coated with alpha-fetoprotein monoclonal antibody, and shake well; repeat steps 3) to 5) to obtain a concentration of alpha-fetoprotein;

7) obtain a percentage of alpha-fetoprotein variant by the data processing module.

EXAMPLE 7

The method for separating and detecting an alpha-fetoprotein variant provided by Example 6 only comprises steps 1) and 6), and can directly detect the concentration of alpha-fetoprotein.

EXAMPLE 8

The method for separating and detecting an alpha-fetoprotein variant provided by the present invention employs the aforesaid separation and detection system to detect a percentage of an alpha-fetoprotein variant, comprising the following steps:

1) adding sample add a sample of hemolytic serum, plasma, or whole blood to the separation and detection system or added to the sample wells provided by the aforesaid reagent card.

2) separating the alpha-fetoprotein variant add the sample to a reagent tank containing magnetic particle coupling a lectin, shake well;

concentrate the magnetic particle by a magnetic separation module and discard the liquid;

add the concentrated magnetic particle to a reagent tank containing a cleaning solution, shake well;

add the cleaned magnetic particle to a reagent tank containing an eluent, shake well, and concentrate the magnetic particle by the magnetic separation module, to obtain an alpha-fetoprotein variant eluent;

3) incubation add the alpha-fetoprotein variant eluent to a reaction cup containing magnetic particle coated with alpha-fetoprotein monoclonal antibody, and meanwhile add an enzyme-labeled anti-alpha-fetoprotein antibody pre-packed in another reagent tank, to undergo incubation.

4) concentration concentrate the magnetic particle by the magnetic separation module, and discard the liquid;

5) cleaning add the concentrated magnetic particle to a reagent tank containing a cleaning solution, shake well, and repeat step 4);

6) color development add the concentrated magnetic particle to a luminol substratepre-packed in another reagent tank, and obtain a concentration of alpha-fetoprotein heterosomes by a data processing module.

7) at the same time with 2), the system adds a sample to a reagent tank containing magnetic particles coated with alpha-fetoprotein monoclonal antibody, repeat steps 3) and 6) to obtain the concentration of alpha-fetoprotein;

8) obtain a percentage of alpha-fetoprotein variant by the data processing module.

Logical algorithm of the percentage of alpha-fetoprotein variant by the data processing module: after determining the serial number of a sample, the instrument will retrieve concentration of alpha-fetoprotein and concentration of alpha-fetoprotein variant for the same sample, and then calculate the percentage of AFP-L3 in AFP, thereby calculating the AFP-L3 content, i.e., AFP-L3%.

The foregoing description shows and describes preferred embodiments of the present invention. As described above, it should be understood that the present invention is not limited to the forms disclosed herein and should not be construed as an exclusion of other embodiments but may be used in a variety of other combinations, modifications and the environment, and may be modified within the scope of the inventive concept described herein, by the teachings or techniques or knowledge of the related art. Besides, modifications and changes made by one skilled in the art without departing from the spirit and scope of the present invention should be within the scope of the appended claims.

The invention claimed is:

1. A separation and detection kit for an alpha-fetoprotein variant AFP-L3, comprising a separation reagent, a detection reagent and a reaction plate, wherein the separation reagent comprises a magnetic particle coupling a lectin, and an eluent, wherein the surface of the magnetic particle coupling the lectin is covered with an epoxy resin, the magnetic particle coupling the lectin specifically binds to the alpha-fetoprotein variant AFP-L3 in a sample;

the detection reagent comprises a magnetic particle coated with an anti-alpha-fetoprotein antibody and an enzyme-labeled anti-alpha-fetoprotein antibody; and the reaction plate is in a form of a card and comprises a reagent tank and a reaction well.

2. The separation and detection kit according to claim 1, wherein the separation reagent further comprises a protective solution, and the detection reagent further comprises a buffer.

3. The separation and detection kit according to claim 2, wherein the protective solution is 0.02 M PBS pH 7.4, 0.5% BSA and 0.1 M D-mannoside.

4. The separation and detection kit according to claim 2, wherein the buffer is 0.02 M PBS, 10% bovine serum and 0.1% proclin-300.

5. The separation and detection kit according to claim 1 wherein the separation reagent or the detection reagent further comprises a cleaning solution.

6. The separation and detection kit according to claim 5, wherein the cleaning solution in the separation reagent is 20 mM Tris-HCl and 0.5M D-mannoside.

7. The separation and detection kit according to claim 5, wherein the cleaning solution in the detection reagent is a 1% Tween 20 solution prepared in PBS pH 7.4.

8. A separation and detection system for alpha-fetoprotein variant, comprising:
   a magnetic separation module for separating magnetic particle from a liquid;
   a detection module for detecting an alpha-fetoprotein variant and an alpha-fetoprotein content;
   a data processing module for calculating a ratio of the alpha-fetoprotein variant to the alpha-fetoprotein; and
   the separation and detection kit according to claim 1;
   the magnetic separation module using the separation reagent in the separation and detection kit for accomplishing the separation of alpha-fetoprotein variant;
   the detection module using the detection reagent in the separation and detection kit for accomplishing the detection of the alpha-fetoprotein variant content and alpha-fetoprotein content.

9. The separation and detection system according to claim 8, wherein, when the separation and detection system is selected to detect the alpha-fetoprotein content, the magnetic separation module does not use the separation reagent, and the detection means detects the content of alpha-fetoprotein in a sample to be detected;
   when the separation and detection system is selected to detect the alpha-fetoprotein variant content, the magnetic separation module separates the alpha-fetoprotein variant in the sample to be detected, and the detection module detects the content of the alpha-fetoprotein variant in the sample to be detected;
   when the separation and detection system is selected to detect a percentage of the alpha-fetoprotein variant, the magnetic separation module separates the alpha-fetoprotein variant in the sample to be detected, the detection module detects the content of alpha-fetoprotein variant and the content of the alpha-fetoprotein in the sample to be detected, and the data processing module calculates the percentage of the alpha-fetoprotein variant.

10. A method for separating and detecting an alpha-fetoprotein variant using the separation and detection kit according to claim 1, the method comprising:
    a separating step of contacting lectin-labeled magnetic particle with the sample so as to bind to an alpha-fetoprotein variant AFP-L3;
    an eluting step of separating the magnetic particle and eluting the alpha-fetoprotein variant AFP-L3; and
    a detecting step of detecting the alpha-fetoprotein variant AFP-L3 by using an AFP immunoassay method.

11. The method for separating and detecting an alpha-fetoprotein variant according to claim 10, wherein the AFP immunoassay method is a magnetic particle chemiluminescence method.

12. The separation and detection kit according to claim 1,
    wherein the eluent is 0.02 M PBS (pH 7.0), 5M D-mannoside; and
    the lectin is *lens culinaris* agglutinin or concanavalin lectin.

13. The separation and detection kit according to claim 1, wherein the anti-alpha-fetoprotein antibody is a monoclonal antibody against alpha-fetoprotein.

* * * * *